United States Patent
Tanaka et al.

(10) Patent No.: US 9,081,013 B2
(45) Date of Patent: Jul. 14, 2015

(54) MARKER FOR DETECTING GASTRIC CANCER AND METHOD FOR DETECTING GASTRIC CANCER

(75) Inventors: Yoshinori Tanaka, Kanagawa (JP); Satoko Kanamori, Kanagawa (JP); Michimoto Kobayashi, Kanagawa (JP); Giman Jung, Kanagawa (JP); Yoshiharu Sakai, Kyoto (JP); Hiroshi Okabe, Kyoto (JP)

(73) Assignees: TORAY INDUSTRIES, INC., Tokyo (JP); KYOTO UNIVERSITY, Kyoto-Shi (JP)

( * ) Notice: Subject to any disclaimer, the term of this patent is extended or adjusted under 35 U.S.C. 154(b) by 7 days.

(21) Appl. No.: 13/582,316

(22) PCT Filed: Mar. 3, 2011

(86) PCT No.: PCT/JP2011/054866
§ 371 (c)(1),
(2), (4) Date: Aug. 31, 2012

(87) PCT Pub. No.: WO2011/108628
PCT Pub. Date: Sep. 9, 2011

(65) Prior Publication Data
US 2012/0329074 A1    Dec. 27, 2012

(30) Foreign Application Priority Data
Mar. 3, 2010 (JP) ................................. 2010-046613

(51) Int. Cl.
*G01N 33/53* (2006.01)
*G01N 33/574* (2006.01)

(52) U.S. Cl.
CPC .. *G01N 33/57446* (2013.01); *G01N 2333/4712* (2013.01)

(58) Field of Classification Search
None
See application file for complete search history.

(56) References Cited

U.S. PATENT DOCUMENTS

| | | | |
|---|---|---|---|
| 5,420,016 A * | 5/1995 | Boguslaski et al. | 435/12 |
| 2003/0175288 A1 | 9/2003 | Itoh | |
| 2010/0075354 A1 | 3/2010 | Sato et al. | |
| 2011/0294136 A1 | 12/2011 | Meyer et al. | |

FOREIGN PATENT DOCUMENTS

| | | |
|---|---|---|
| WO | WO 02/10369 A1 | 2/2002 |
| WO | WO 2008/064670 A2 | 6/2008 |
| WO | WO 2008/099972 A1 | 8/2008 |
| WO | WO 2010/053816 A2 | 5/2010 |
| WO | WO 2011/094759 A2 | 8/2011 |

OTHER PUBLICATIONS

Jeong et al. Proteomic Analysis of Human Small Cell Lung Cancer Tissues: Up-Regulation of Coactosin-Like Protein-1, Journal of Proteome Research, 10, pp. 269-276, Published online Nov. 2010.*

Kim et al., Identification of replicative senescence-associated genes in human umbilical vein endothelial cells by an annealing control primer system, Experimental Gerontology,43, pp. 286-295, Published online Jan. 2008.*
LaBaer, So, You want to look for biomarkers, Journal of Proteome Research, 4, pp. 1053-1059, Published online Jun. 2005.*
Mayeux, Biomarkers: Potential Uses and Limitations, NeuroRX, vol. 1, Issue 2, pp. 182-188, Apr. 2004.*
Qi et al., Effects of different peptide fragments derived from proadrenomedullin on gene expression of adrenomedullin gene, Peptides, vol. 23, Issue 6, pp. 1141-1147, Jun. 2002.*
International Search Report, issued in PCT/JP2011/054866, dated Apr. 5, 2011.
Nakatsura et al., "Cellular and humoral immune responses to a human pancreatic cancer antigen, coactosin-like protein, originally defined by the SEREX method", Eur. J. Immunol, 2002, 32 (3), pp. 826-836.
Nakatsura et al., "Gene Cloning of Immunogenic Antigens Overexpressed in Pancreatic Cancer", Biochemical and Biophysical Research Communications, 281 (4), 2001, pp. 936-944.
Nakatsura et al., "Identification of Tumor Rejection Antigen Recognized by Human T Lymphocyte", Sagawa Sentan Kagaku Gijutsu Shinko Zaidan Josei Kenkyu Hokokusho, Dai 14, Kai, 2001, pp. 7-11.
Extended European Search Report for European Application No. 11750737.6 dated Jun. 26, 2013.
International Search Report for International Application No. PCT/JP2012/071654 dated Dec. 11, 2012.
International Search Report for International Application No. PCT/JP2012/071662 dated Dec. 11, 2012.
Provost et al., "Coactosin-like protein, a human F-actin-binding protein: critical role of lysine-75", Biochem J., vol. 359, 2001, pp. 255-263, XP055066565.
Carpelan-Holmstrom, M. et al, "Preoperatvie serum levels of CEA and CA 242 in colorectal cancer," British Journal of Cancer, 1995, vol. 71, pp. 868-872.
Lee, C.H. et al, "Identification of the heterogeneous nuclear ribonucleoprotein A2/B1 as the antigen for the gastrointestinal cancer specific monoclonal antibody MG7," Proteomics, 2005, vol. 5, pp. 1160-1166.

(Continued)

*Primary Examiner* — Jacob Cheu
(74) *Attorney, Agent, or Firm* — Birch, Stewart, Kolasch & Birch, LLP

(57) ABSTRACT

It is intended to provide a method for detecting gastric cancer, which is low invasive to a human test subject and has high detection sensitivity and accuracy. The present invention provides a method comprising measuring in vitro the amount of COTL1 protein, a variant thereof, and/or a fragment thereof in a body fluid sample derived from a human test subject, and detecting the presence or absence of gastric cancer affecting the test subject on the basis of the amount, and a kit for gastric cancer diagnosis comprising an antibody capable of specifically binding to the protein.

6 Claims, 2 Drawing Sheets

(56) References Cited

OTHER PUBLICATIONS

Melle, C. et al, "Characterization of Pepsinogen C as a Potential Biomarker for Gastric Cancer Using a Histo-Proteomic Approach," Journal of Proteome Research, 2005, vol. 4, pp. 1799-1804.

Quillien, V. et al, "Comparison of Cyfra 21-1, TPA and SCC tumor markers in esophageal squamous cell carcinoma," Onocology Reports, 1998, vol. 5, pp. 1561-1565.

Ryu, J.W. et al, "The Proteomics Approach to Find Biomarkers in Gastric Cancer," J. Korean Med. Sci., 2003, vol. 18, pp. 505-509.

* cited by examiner

MARKER FOR DETECTING GASTRIC CANCER AND METHOD FOR DETECTING GASTRIC CANCER

TECHNICAL FIELD

The present invention relates to a method for detecting gastric cancer by measuring the concentration of COTL1 protein as a marker for detecting gastric cancer in a body fluid.

The present invention also relates to a kit for detecting gastric cancer comprising a substance capable of binding to the protein used for detecting gastric cancer.

BACKGROUND ART

The stomach is an important organ of the digestive system that plays a role in storing food or drink for several hours during which the food or drink is rendered acidic by the action of secreted gastric acid and thereby prevented from spoiling while it is digested by digestive enzymes.

Gastric cancer occurs at a frequency of approximately 50 to 60 per 100,000 population in Japan and is more common in males than in females with a male-to-female ratio of 1 to 2:1. Also, gastric cancer kills approximately 50,000 people a year, which account for approximately 17% of the number of deaths caused by all cancer types, and was thus ranked No. 1 in the site-specific cancer mortality until the early 1990s after World War II. Gastric cancer is now ranked No. 2 following lung cancer, as the number of patients has been declining every year. Still, many patients suffer from this disease. On a world scale, gastric cancer affects many patients in Asian countries, such as Japan, South Korea, and China, and in South America. Examples of risk factors of gastric cancer can generally include smoking, high-salt diets, and infection with *Helicobacter pylori*.

Endoscopic therapy, surgery, chemotherapy, radiation therapy, and the like are known as the treatment of gastric cancer and performed in consideration of disease stage, tumor size/depth, the degree of metastasis, etc. The course of treatment is determined on the basis of the "Gastric Cancer Treatment Guidelines" prepared by the Japanese Gastric Cancer Association in 2004. Early gastric cancer can be completely resected endoscopically or surgically and also has a low rate of recurrence. Advanced gastric cancer, on the other hand, recurs in many cases, even after extirpation of lesions, due to micrometastasis that has not been found at the time of operation. Gastric cancer provides a relatively favorable prognosis when found at an early stage, and typically, 90% or more cases are completely healed. However, the outcome of large tumor or after metastasis has a poor 5-year survival rate of approximately 70%. Hence, its early detection is important.

Unfortunately, most cases of gastric cancer have no symptoms at an early stage and do not produce recognizable subjective symptoms until the cancer is advanced. Thus, gastric cancer is difficult to early detect based on subjective symptoms. With the progression of gastric cancer, loose stool, black stool, nausea, gastric distress, and the like are found as subjective symptoms, and fatigability, fever, weight loss, anemia, and the like are found as systemic symptoms. In a more advanced stage, a lump is felt in the abdominal region as tumor increases in size. Even after appearance of such subjective symptoms, patients tend to often neglect them, and in many cases, already advanced cancer is detected by radiography or the like during medical examination. Hence, it is important to develop an examination method for highly sensitively and accurately detecting gastric cancer at an early stage.

Gastric cancer can be examined by a diagnostic imaging method such as ultrasonography, CT scan, angiography, or radiography. The diagnostic imaging method is useful in detecting small tumor in early gastric cancer, but is less than efficient when directed to many human test subjects, for example, in medical check-up, and disadvantageously requires relatively high cost for diagnosis.

With technical progress on genomics or proteomics in recent years, various novel tumor marker candidates have been being found as a result of research in the cancer field (e.g., Patent Literatures 1 and 2). Since a highly sensitive marker in blood specific for particular cancer probably allows relatively inexpensive high-throughput examination or diagnosis, its development is strongly demanded. Examples of methods for searching for a marker include a method involving comparing gene expression or the amount of proteins or cell metabolites or the like between cancer cells and non-cancerous cells, and a method involving measuring the amount of mRNA, proteins, or metabolites or the like contained in the body fluids of cancer patients and patients without cancer. For example, CEA, BFP, NCC-ST-439, CA72-4, and CA19-9 are known as tumor markers for gastric cancer currently used in clinical setting. Also, marker candidates have been found histologically, such as pepsinogen C (Non Patent Literature 1), hnRNP A2/B1 (Non Patent Literature 2), NSP3, transgelin, prohibitin, HSP27, protein disulfide isomerase A3, and GRP58 (Non Patent Literature 3). Unfortunately, these markers and marker candidates have poor specificity and/or detection sensitivity, or efficient methods for detecting them from biological samples have not yet been established. Thus, use thereof is limited to a narrow range of purposes such as posttreatment follow-up. Hence, a gastric cancer marker having higher specificity and detection sensitivity is desired.

CITATION LIST

Patent Literature

Patent Literature 1: International Publication No. WO2005/001126
Patent Literature 2: International Publication No. WO2003/060121

Non Patent Literature

Non Patent Literature 1: Melle, C. et al., Journal of proteome research, 2005, Vol. 5, p. 1799-1804
Non Patent Literature 2: Lee, C. et al., Proteomics, 2005, Vol. 5, p. 1160-1166
Non Patent Literature 3: Ryu, J. W. et al., Journal Korean Medical Science, 2003, Vol. 18, p. 505-509

SUMMARY OF INVENTION

Technical Problem

An object of the present invention is to provide a tumor marker useful in detecting gastric cancer and a method for detecting gastric cancer using the tumor marker.

Solution to Problem

In order to attain the object, the present inventors have compared protein groups present in the blood of gastric cancer patients and the blood of normal individuals to find COTL1 protein as a novel tumor marker detected in the blood of gastric cancer patients. Based on the findings, the present invention has been completed.

The "COTL1" (coactosin-like 1) protein, an actin cytoskeleton-binding protein, has been reported to bind to 5-lipoxygenase in cells and considered to participate in leukotriene biosynthesis (Provost P. et al., 2001, Journal of Biological Chemistry, Vol. 276, p. 16520-16527). This protein has also been reported to exhibit a serum concentration increased by the onset of rheumatism (Eun-Heui J. et al., 2009, Experimental and Molecular Medicine, Vol. 41, p. 354-361). This protein is further known to be highly expressed in pancreatic cancer tissues (Nakatsura T. et al., 2001, Biochemical and Biophysical Research Communication, Vol. 256, p. 75-80). However, the relation of the COTL1 protein to gastric cancer has neither been reported nor known so far.

Thus, the present invention encompasses the following aspects.

(1) A method for detecting gastric cancer, comprising measuring in vitro the amount of a marker for detecting gastric cancer consisting of COTL1 protein, a variant thereof, and/or a fragment thereof present in a body fluid derived from a test subject, and determining whether or not the test subject has gastric cancer on the basis of the amount.

(2) The method according to (1), wherein the COTL1 protein is a polypeptide shown in SEQ ID NO: 1.

(3) The method according to (1) or (2), wherein when the amount of the marker for detecting gastric cancer in the test subject is statistically significantly larger than that of a normal individual, the test subject is determined to have gastric cancer.

(4) The method according to (3), wherein the statistically significantly larger amount is two or more times that of a normal individual.

(5) The method according to any of (1) to (4), wherein the measurement is performed using a substance capable of specifically binding to the marker for detecting gastric cancer.

(6) The method according to (5), wherein the substance capable of binding is an anti-COTL1 antibody, an anti-COTL1 variant antibody, and/or a fragment thereof.

(7) The method according to any of (1) to (6), wherein the gastric cancer is early gastric cancer.

(8) The method according to any of (1) to (7), wherein the body fluid sample is blood or urine.

(9) A kit for detecting gastric cancer comprising an anti-COTL1 antibody, an anti-COTL1 variant antibody, a fragment thereof, and/or a chemically modified derivative thereof.

The present specification encompasses the contents described in the specification and/or drawings of Japanese Patent Application No. 2010-046613 which serves as a basis for the priority of the present application.

Advantageous Effects of Invention

According to the present invention, gastric cancer can be detected easily with high reliability. For example, the presence or absence of gastric cancer can be determined easily just by the measurement of the concentration of COTL1 protein contained in a body fluid sample such as the blood of a gastric cancer patient. The method for detecting gastric cancer of the present invention is effective because it can detect even early cancer.

DESCRIPTION OF EMBODIMENTS

Figure 1:
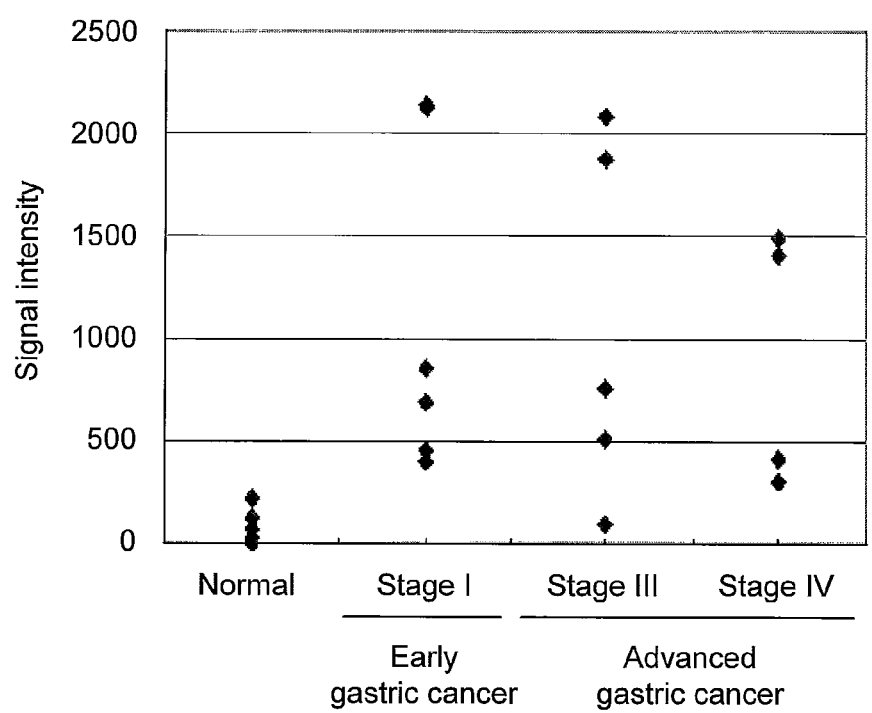
FIG. 1 is a graph showing results of detecting COTL1 protein in the plasma of gastric cancer patients and normal human individuals by Western blotting.

1. Marker for Detecting Gastric Cancer (Summary)

The first aspect of the present invention relates to a marker for detecting gastric cancer that is intended for the detection of gastric cancer. The present invention is based on the findings that the COTL1 protein is more abundant in the blood of gastric cancer patients than that of normal human individuals. As described in the second aspect of the present invention below, gastric cancer affecting a test subject can be detected depending on the increased amount of this protein present in the blood of the test subject.

(Constitution of Invention)

In the present invention, the "marker for detecting gastric cancer" is a biological marker intended for the detection of gastric cancer and refers to a substance that serves as an index showing that the test subject has gastric cancer. The marker for detecting gastric cancer of the present invention is constituted of COTL1 protein, a variant thereof, and/or a fragment thereof (hereinafter, they may be collectively referred to as "COTL1 protein, etc." in the present specification).

The "COTL1 protein" of the present invention refers to an actin cytoskeleton-binding protein, as described above. In the present invention, the COTL1 protein corresponds to any of approximately 17 kDa COTL1 proteins of various organism species composed of 142 amino acids and is preferably human-derived COTL1 protein (GenBank Accession No. NP 066972.1), specifically, a polypeptide shown in SEQ ID NO: 1. Also, the COTL1 protein may be a variant of the COTL1 protein, particularly the human-derived COTL1 protein, and/or fragment(s) of the wild-type and/or variant COTL1 proteins. The present inventors have revealed that the COTL1 protein, etc. is produced by gastric cancer cells and leaked out in a larger amount into the body fluids of gastric cancer patients than those of normal individuals.

In the present specification, the "variant" of the COTL1 protein means a variant comprising an amino acid sequence derived from an amino acid sequence of the COTL1 protein, preferably the human-derived wild-type COTL1 protein shown in SEQ ID NO: 1, or its partial sequence, by the deletion, substitution, addition, or insertion of one or more, preferably one to several amino acids, or a variant that exhibits % identity of approximately 80% or higher, approximately 85% or higher, preferably approximately 90% or higher, more preferably approximately 95% or higher, approximately 97% or higher, approximately 98% or higher, or approximately 99% or higher, to the amino acid sequence or its partial sequence. In this context, the term "several" refers to an integer of approximately 10, 9, 8, 7, 6, 5, 4, 3, or 2 or smaller. The "% identity" can be determined with or without a gap introduction using a BLAST- or FASTA-based protein search system (Karlin, S. et al., 1993, Proceedings of the National Academic Sciences U.S.A., Vol. 90, p. 5873-5877; Altschul, S. F. et al., 1990, Journal of Molecular Biology, Vol. 215, p. 403-410; and Pearson, W. R. et al., 1988, Proceedings of the National Academic Sciences U.S.A., Vol. 85, p. 2444-2448). Specific examples of the variant of the COTL1 protein include variants having a polymorphism (including SNIPs) based on the type of a test subject (e.g., the race of a human test subject) or an individual, and splicing variants.

In the present specification, the "fragment" refers to a polypeptide fragment that consists of consecutive amino acid residues from at least 7 or more to less than all, at least 10 or more to less than all, at least 15 or more to less than all, preferably at least 20 or more to less than all, at least 25 or more to less than all, more preferably at least 35 or more to less than all, at least 40 or more to less than all, or at least 50 or more to less than all of amino acids constituting the wild-type COTL1 protein, preferably the human-derived wild-type COTL1 protein shown in SEQ ID NO: 1, or the variant thereof, and retains one or more epitopes. Such a fragment can immunospecifically bind to an antibody according to the present invention or a fragment thereof described below. Such a peptide fragment is encompassed by the COTL1 protein because: the object of the present invention can be attained as long as the COTL1 protein, albeit fragmented, in blood can be quantified; and the full-length polypeptide of the wild-type COTL1 protein (preferably the human-derived wild-type COTL1 protein shown in SEQ ID NO: 1) or the variant thereof may be found fragmented in blood by the action of, for example, protease or peptidase, present in the blood.

2. Method for Detecting Gastric Cancer (Summary)

The second aspect of the present invention relates to a method for detecting gastric cancer. The method of the present invention is based on the findings that the COTL1 protein is more abundant in the blood of gastric cancer patients than that of normal human individuals, and involves measuring the amount of the marker for detecting gastric cancer of the present invention present in a body fluid derived from a test subject and detecting gastric cancer on the basis of the results.

(Constitution of Invention)

The method of the present invention comprises (1) a measurement step of the marker for detecting gastric cancer and (2) an affection determination step. Hereinafter, each step will be described in detail.

2-1. Measurement Step of Marker for Detecting Gastric Cancer

The "measurement step of the marker for detecting gastric cancer" is the step of measuring in vitro the amount of the marker for detecting gastric cancer of the present invention, i.e., COTL1 protein, a variant thereof, and/or a fragment thereof, present in a body fluid derived from a test subject.

In the present specification, the "test subject" refers to a specimen subjected to the detection of gastric cancer affecting the individual and corresponds to a vertebrate, preferably a mammal, particularly preferably a human. Hereinafter, the human serving as the test subject is particularly referred to as a "human test subject" in the present specification.

In the present specification, the "body fluid" is a sample subjected to detecting gastric cancer and means a biological fluent material. The body fluid is not particularly limited and may be any biological fluent material possibly containing the marker for detecting gastric cancer of the present invention. Examples thereof include blood, urine, culture supernatants of lymphocytes, spinal fluid, digestive juice (including gastric juice and saliva), sweat, ascitic fluid, runny nose, tear, vaginal fluid, and seminal fluid. Blood or urine is preferable. In this context, the "blood" encompasses whole blood, plasma, and serum. The whole blood may be any of venous blood, arterial blood, and cord blood. The body fluid may be a combination of two or more different body fluids obtained from one individual. The method for detecting gastric cancer of the present invention is very useful as a convenient detection method because it is capable of detection even from blood or urine with low invasiveness.

The "body fluid derived from a test subject" refers to a body fluid that has already been collected from the test subject. The operation itself of collecting the body fluid is not encompassed by the aspect of the present invention. The body fluid derived from a test subject may be subjected to the method of the present invention immediately after being collected from the test subject. Alternatively, the body fluid thus collected may be refrigerated or frozen in itself or after appropriate treatment, brought to room temperature in use, and then subjected to the method of the present invention. Examples of the appropriate treatment before refrigeration or freezing include: the addition of heparin or the like for anticoagulation treatment to whole blood; and the separation of plasma or serum. Such treatment can be performed on the basis of a technique known in the art.

In the present specification, the "amount of the marker for detecting gastric cancer of the present invention" refers to the quantity of the COTL1 protein, etc. present in the body fluid derived from a test subject. This quantity may be any of absolute and relative amounts. The absolute amount corresponds to the mass or volume of the marker for detecting gastric cancer contained in the predetermined amount of the body fluid. The relative amount refers to a relative value indicated by the measured value of the test subject-derived marker for detecting gastric cancer compared with a particular measured value. Examples thereof include concentration, fluorescence intensity, and absorbance.

The amount of the marker for detecting gastric cancer can be measured in vitro using a method known in the art. Examples thereof include a measurement method using a substance capable of specifically binding to the protein, etc.

In the present specification, the phrase "capable of specifically binding" means that a certain substance forms a complex substantially only with the marker for detecting gastric cancer, i.e., the COTL1 protein, the variant thereof, and/or the fragment thereof, used as the target of the present invention. In this context, the term "substantially" means binding other than nonspecific binding.

Examples of "substance capable of specifically binding" include COTL1-binding proteins. More specifically, the substance capable of specifically binding is, for example, an "anti-COTL1 antibody" recognizing and binding to the COTL1 protein as an antigen, preferably an antibody recognizing and binding to the polypeptide having the amino acid sequence shown in SEQ ID NO: 1, an "anti-COTL1 variant antibody" recognizing and binding to the variant of the COTL1 protein as an antigen, preferably an antibody recognizing and binding to a polypeptide having a variant amino acid sequence of the sequence of SEQ ID NO: 1, and/or an antibody fragment thereof. Alternatively, the substance capable of specifically binding may be a chemically modified derivative thereof. In this context, the "chemically modified derivative" contains any of a functional modification necessary for acquiring or retaining the specific binding activity of the anti-COTL1 antibody, the anti-COTL1 variant antibody, and/or the fragment thereof against the COTL1 protein, etc. and a modification for labeling necessary for detecting the anti-COTL1 antibody, the anti-COTL1 variant antibody, and/or the fragment thereof.

Examples of the functional modification include glycosylation, deglycosylation and PEGylation.

Examples of the labeling modification include labeling with a fluorescent dye (FITC, rhodamine, Texas Red, Cy3, or Cy5), a fluorescent protein (e.g., PE, APC, and GFP), an enzyme (e.g., horseradish peroxidase, alkaline phosphatase, and glucose oxidase), or biotin or (strept)avidin.

The antibody may be any of polyclonal and monoclonal antibodies. The monoclonal antibody is preferable for achieving specific detection. The anti-COTL1 polyclonal antibody, etc. (including an anti-COTL1 polyclonal antibody, an anti- COTL1 variant polyclonal antibody, and/or polyclonal antibody(s) comprising antibody fragment thereof) or the monoclonal antibody, etc. (including an anti-COTL1 monoclonal antibody, an anti-COTL1 variant monoclonal antibody, and/or monoclonal antibody(s) comprising antibody fragment(s) thereof) specifically binding to the COTL1 protein, etc. can be prepared by a method described below. In addition, an anti-human COTL1 polyclonal antibody is commercially available from Proteintech Group Inc., etc., and may be used in the present invention. The globulin type of the antibody of the present invention is not particularly limited as long as it has the features described above. The globulin type of the antibody may be any of IgG, IgM, IgA, IgE, and IgD and is preferably IgG and IgM. Examples of the antibody fragment include, but not limited to, Fab, Fab', F(ab')$_2$, Fv, and ScFv. The antibody of the present invention also encompasses an antibody fragment and a derivative that can be produced by a genetic engineering technique. Examples of such an antibody include synthetic antibodies, recombinant antibodies, multispecific antibodies (including bispecific antibodies), and single-chain antibodies. The anti-COTL1 protein antibody, etc. of the present invention is an antibody against one or more epitopes each consisting of at least 5, preferably at least 8 amino acids of the protein. The specific polyclonal antibody can be prepared, for example, by an approach involving applying the antiserum of a rabbit or the like immunized with the protein to a column comprising the COTL1 protein, etc. conjugated with a carrier such as agarose, and collecting IgG antibodies bound to the column carrier.

(1) Preparation of Anti-COTL1 Antibody

Hereinafter, methods for preparing the anti-COTL1 polyclonal antibody, etc. and monoclonal antibody, etc. used in the present invention will be described specifically.

(1-1) Preparation of Immunogen

For the antibody preparation in the present invention, COTL1 protein, etc. is prepared as an immunogen (antigen). The COTL1 protein that can be used as an immunogen in the present invention is, for example, human COTL1 protein having the amino acid sequence shown in SEQ ID NO: 1 or a variant thereof, or a polypeptide fragment thereof, or a fusion polypeptide thereof with an additional peptide (e.g., a signal peptide, a labeling peptide, etc.). When a COTL1 protein fragment is used as the COTL1 protein serving as an immunogen, this COTL1 protein fragment for use as an immunogen can be synthesized, for example, by an approach known in the art, for example, a solid-phase peptide synthesis method, using information about the amino acid sequence of SEQ ID NO: 1. When the COTL1 protein fragment is used as an immunogen, it is preferable to use a COTL1 protein fragment linked to a carrier protein such as KLH or BSA.

Also, the COTL1 protein, etc. serving as an immunogen can be obtained using a DNA recombination technique known in the art. cDNA encoding the COTL1 protein, etc. can be prepared by a cDNA cloning method. Total RNA is extracted from biological tissues such as gastric epithelial cells expressing the gene of immunogenic COTL1, etc. and treated with an oligo-dT cellulose column. A cDNA library can be prepared by RT-PCR from the obtained poly-A(+) RNA and screened by hybridization screening, expression screening, antibody screening, or the like to obtain the cDNA clone of interest. The cDNA clone may be further amplified by PCR, if necessary. As a result, cDNA corresponding to the gene of interest can be obtained. Such a cDNA cloning technique is described in, for example, Sambrook, J. and Russell, D., Molecular Cloning, A LABORATORY MANUAL, Cold Spring Harbor Laboratory Press, issued on Jan. 15, 2001, Vol. 1, 7.42 to 7.45 and Vol. 2, 8.9 to 8.17.

Subsequently, the cDNA clone thus obtained is incorporated in expression vectors, with which prokaryotic or eukaryotic host cells are transformed or transfected. These cells can be cultured to obtain the COTL1 protein, etc. of interest from the cells. When the protein, etc. of interest is obtained from the culture supernatant thereof, a nucleotide sequence encoding a secretory signal sequence can be flanked by the 5' end of DNA encoding the polypeptide to thereby extracellularly secrete a mature polypeptide.

Examples of the expression vectors include *E. coli*-derived plasmids (e.g., pET21a, pGEX4T, pC118, pC119, pC18, and pC19), *Bacillus subtilis*-derived plasmids (e.g., pUB110 and pTP5), yeast-derived plasmids (e.g., YEp13, YEp24, and YCp50), and phage DNA such as λ phage (λgt11, λZAP, etc.). In addition, an animal virus such as vaccinia virus or an insect virus vector such as baculovirus may be used. Such vectors and expression systems are available from Novagen, Takara Shuzo Co., Ltd., Daiichi Pure Chemicals Co., Ltd., Qiagen, Stratagene, Promega Corp., Roche Diagnostics, Invitrogen Corp., Genetics Institute, Inc., GE Healthcare, etc.

For example, a method involving first cleaving purified DNA with appropriate restriction enzymes and inserting the resulting fragment to an appropriate restriction or multicloning site to ligate the fragment to the vector is adopted for inserting the cDNA of the COTL1 protein, etc. into each expression vector. The vector can contain, in addition to the DNA encoding the protein, regulatory elements, for example, a promoter, an enhancer, a polyadenylation signal, a ribosome-binding site, a replication origin, a terminator, and a selection marker. Alternatively, a fusion polypeptide may be used, which comprises the polypeptide C- or N-terminally tagged with a labeling peptide for simplified purification of the polypeptide. Examples of the labeling peptide typically include, but not limited to, a histidine repeat of 6 to 10 residues, FLAG, myc peptide, and GFP protein. The DNA recombination technique is described in Sambrook, J. & Russell, D. (described above). DNA ligase known in the art is used in the ligation of the DNA fragment with the vector fragment.

Prokaryotic cells such as bacteria (e.g., *Escherichia coli* and *Bacillus subtilis*), yeast (e.g., *Saccharomyces cerevisiae*), insect cells (e.g., Sf cells), mammalian cells (e.g., COS, CHO, and BHK), or the like can be used as host cells. A method for introducing the recombinant vectors to host cells is not particularly limited as long as the DNA can be introduced to each host by the method. Examples of the method for introducing the vectors to bacteria include a heat shock method, a method using calcium ions, and electroporation. These techniques are known in the art and described in various documents. See, for example, Sambrook, J. et. al., (1989) Molecular Cloning: A Laboratory Manual, Second Ed., Cold Spring Harbor Laboratory Press, Cold Spring Harbor, N.Y. Alternatively, for example, a Lipofection method (PNAS (1989) Vol. 86, 6077; and PNAS (1987) Vol. 84, 7413), electroporation, a calcium phosphate method (Virology (1973) Vol. 52, 456-467), a method using liposomes, or a DEAE-dextran method is preferably used for introducing the vectors to animal cells.

Any of natural and synthetic media may be used as a medium for the culture of transformants obtained with microbes (such as *E. coli* or yeast) as hosts as long as it contains a carbon source, a nitrogen source, inorganic salts, etc., utilizable by the microbes and permits efficient culture of the transformants. The culture is usually performed at 37° C. for 6 to 24 hours under aerobic conditions such as shake culture or aeration stirring culture. During the culture period, the pH is kept around the neutral value. The pH is adjusted using an inorganic or organic acid, an alkaline solution, or the like. An antibiotic such as ampicillin or tetracycline may be added to the medium, if necessary, during the culture. Transformants such as mammalian cells are also cultured in a medium suitable for each type of cells, and proteins produced in the culture supernatant or the cells are then collected. In this procedure, the medium may or may not contain serum. A serum-free medium is more preferable for this culture. When the COTL1 protein, etc. is produced within bacteria or cells, these bacteria or cells are disrupted to extract proteins. Alternatively, when the COTL1 protein, etc. is produced outside bacteria or cells, the culture solution is directly used or the bacteria or cells are removed by centrifugation or the like.

When the protein according to the present invention is produced in a form untagged with a labeling peptide, examples of its purification method can include a method based on ion-exchange chromatography. This method may be used in combination with gel filtration, hydrophobic chromatography, isoelectric chromatography, or the like. On the other hand, examples of the purification method for the protein tagged with a labeling peptide such as a histidine repeat, FLAG, myc, or GFP can include a method based on affinity chromatography suitable for each labeling peptide generally used. It is preferred to construct expression vectors that achieve simplified isolation and purification. Particularly, the expression vectors are constructed so that the polypeptide is expressed in the form of a fusion protein with the labeling peptide. This protein can be prepared in a genetic engineering manner to thereby simplify isolation and purification. Whether or not the COTL1 protein, etc. is obtained can be confirmed by SDS-polyacrylamide gel electrophoresis or the like.

(1-2) Preparation of Antibody

The COTL1 protein, etc. thus obtained can be used as an antigen to obtain an antibody specifically recognizing the COTL1 protein, etc.

More specifically, the protein, the protein fragment, the protein variant, the fusion protein, or the like contain antigenic determinant(s) or epitope(s) that induce antibody formation. These antigenic determinants or epitopes may be linear or a higher order structure (discontinuous). The antigenic determinants or epitopes can be identified by any method known in the art.

The protein of the present invention can induce any aspect of the antibodies. Any of polyclonal and monoclonal antibodies can be prepared using a routine technique as long as the whole of or a portion of the protein or its epitope is isolated. Examples of methods therefor include those listed in Kennet et al., ed., Monoclonal Antibodies, Hybridomas: A New Dimension in Biological Analyses, Plenum Press, New York, 1980.

(1-2-1) Preparation of Polyclonal Antibody

For the polyclonal antibody preparation, the obtained COTL1 protein, etc. is first dissolved in a buffer to prepare an immunogen. An adjuvant may be added, if necessary, for effective immunization. Examples of the adjuvant include a commercially available Freund's complete adjuvant (FCA) and Freund's incomplete adjuvant (FIA). These adjuvants can be used alone or as a mixture.

Next, the immunogen thus prepared is administered to mammals, for example, rats, mice (e.g. Balb/c mice of inbred line), or rabbits, for immunization. One dose of the immunogen is appropriately determined according to the type of animals used in immunization, administration route, etc., and set to approximately 50 to 200 μg per animal. Examples of methods for administering the immunogen include, but not limited to, hypodermic injection using FIA or FCA, intraperitoneal injection using FTA, and intravenous injection using 0.15 mol/L sodium chloride. The immunization interval is not particularly limited. After initial immunization, 2 to 10, preferably 3 to 4 boosters are performed at several-day to several-week intervals, preferably 1- to 4-week intervals. After initial immunization, an antibody titer in the serum of the immunized animals is repetitively measured by ELISA (enzyme-linked immunosorbent assay) or the like. When the antibody titer reaches a plateau, the immunogen is intravenously or intraperitoneally injected thereto for final immunization. Polyclonal antibodies against the COTL1 protein, etc. can be collected from the blood of the animals thus immunized. If the monoclonal antibody is required, anti-COTL1 antibody-producing hybridomas described below can be prepared.

(1-2-2) Preparation of Monoclonal Antibody

Collection of Antibody-Producing Cell from Immunized Animal

According to the present invention, hybridomas producing the anti-COTL1 monoclonal antibody specifically recognizing the COTL1 protein, etc. can be prepared. Such hybridomas can be produced and identified by a routine technique. One method for producing such hybridomas can involve: immunizing animals with the protein of the present invention; collecting antibody-producing cells from the immunized animals; fusing the antibody-producing cells to a myeloma cell line to thereby form hybridoma cells; and identifying hybridomas producing the monoclonal antibody binding to the COTL1 protein, etc. Examples of the antibody-producing cells include spleen cells, lymph node cells, and peripheral blood cells. Spleen cells or local lymph node cells are preferable. These cells can be used after being extracted or collected from the animals immunized with the COTL1 protein, etc. A method for immunizing animals follows the preceding paragraph "Preparation of polyclonal antibody". A generally available established cell line of animals such as mice can be used as the myeloma cell line fused with the antibody-producing cells. It is preferred for the cell line used to have drug selectivity and properties through which the cells cannot survive in an unfused state in a HAT selection medium (containing hypoxanthine, aminopterin, and thymine) but can survive therein only in a state fused with the antibody-producing cells. It is also preferred for the established cell line to be derived from an animal of the same line as in the immunized animals. Specific examples of the myeloma cell line include BALB/c mouse-derived hypoxanthine-guanine phosphoribosyltransferase (HGPRT)-deficient cell lines such as P3×63-Ag.8 (ATCC TIB9), P3×63-Ag.8.U1 (JCRB9085), P3/NSI/1-Ag4-1 (JCRB0009), P3×63Ag8.653 (JCRB0028), and Sp2/0-Ag14 (JCRB0029) lines.

Cell Fusion

For the cell fusion, the antibody-producing cells and the myeloma cell line are mixed at a ratio of approximately 1:1 to 20:1 in a medium for animal cell culture such as a serum-free DMEM or RPMI-1640 medium and subjected to fusion reaction in the presence of a cell fusion promoter. For example, polyethylene glycol having an average molecular weight of 1500 to 4000 daltons can be used as the cell fusion promoter at a concentration of approximately 10 to 80%. In some cases, the cell fusion promoter may be used in combination with an auxiliary agent such as dimethyl sulfoxide for enhanced fusion efficiency. Furthermore, the antibody-producing cells may be fused with the myeloma cell line using a commercially available cell fusion apparatus based on electric stimulation (e.g., electroporation) (Nature, 1977, Vol. 266, 550-552).

Screening and Cloning of Hybridoma

After the cell fusion treatment, the cells were screened for hybridomas producing the anti-COTL1 antibody, etc. of interest. A method therefor involves: appropriately diluting the cell suspension with, for example, a fetal bovine serum-containing RPMI-1640 medium; then inoculating the cells at a concentration of approximately 2,000,000 cells/well onto a microtiter plate; adding a selection medium to each well; and subsequently culturing the cells with the selection medium appropriately replaced. The culture temperature is 20 to 40° C., preferably approximately 37° C. When the myeloma cells are of HGPRT-deficient line or thymidine kinase-deficient line, only hybridomas from the cells having the ability to produce antibodies and the myeloma cell line can be selectively cultured and grown using a selection medium containing hypoxanthine, aminopterin, and thymidine (HAT medium). As a result, the grown cells can be obtained as hybridomas around approximately 14 days into culture in the selection medium.

Next, the culture supernatant of the grown hybridomas is screened to confirm the presence or absence of the antibody of interest. The screening of the hybridomas is not particularly limited and can be performed by a usual method. For example, a portion of the culture supernatant in each well containing the grown hybridomas can be collected and screened by enzyme immunoassay (ETA, and ELISA), radioimmunoassay (RIA), or the like. The fusion cells are cloned by a limiting dilution method or the like. Finally, hybridomas are established as monoclonal antibody-producing cells. The hybridomas of the present invention are stable during culture in a basal medium such as RPMI-1640 or DMEM, as described below, and produce or secrete the monoclonal antibody specifically reacting with the gastric cancer-derived COTL1 protein.

Collection of Antibody

The monoclonal antibody can be collected by a routine technique. Specifically, for example, a usual cell culture or ascitic fluid formation method can be adopted for collecting the monoclonal antibody from the established hybridomas. In the cell culture method, the hybridomas are cultured for 2 to 10 days under usual culture conditions (e.g., 37° C., 5% $CO_2$ concentration) in an animal cell culture medium such as a RPMI-1640 or MEM medium containing 10% fetal bovine serum or a serum-free medium, and the antibody is obtained from the culture supernatant. In the ascitic fluid formation method, approximately 10,000,000 hybridomas are intraperitoneally administered to each animal of the same line as in the mammals from which the myeloma cells are derived so that the hybridomas are grown in large amounts. One to two weeks later, ascitic fluid or serum is collected.

When the method for collecting the antibody requires antibody purification, the purified monoclonal antibody of the present invention can be obtained by appropriately selecting or combining method(s) known in the art such as ammonium sulfate precipitation, ion-exchange chromatography, affinity chromatography, and gel chromatography.

The monoclonal antibody of the present invention encompasses a chimeric antibody, for example, a humanized form of a murine monoclonal antibody. The present invention also provides an antigen-binding fragment of the antibody. Examples of the antigen-binding fragment that can be produced by a routine technique include, but not limited to, Fab and F(ab')$_2$ fragments. The present invention also provides an antibody fragment and a derivative that can be produced by a genetic engineering technique. The antibody of the present invention can be used in assay for detecting the presence of the polypeptide of the present invention or the (poly)peptide fragment thereof both in vitro and in vivo. Moreover, the antibody of the present invention can also be used in the purification of the protein or the protein fragment by immunoaffinity chromatography.

Use of the monoclonal antibody is preferable for achieving specific detection in assay. Even in the case of the polyclonal antibody, specific antibodies can be obtained by a so-called absorption method involving binding antibodies to an affinity column conjugated with purified polypeptides.

(2) In Vitro Measurement of Marker for Detecting Gastric Cancer of the Present Invention Using Anti-COTL1 Antibody, Etc.

Examples of methods for measuring in vitro the amount of the marker for detecting gastric cancer of the present invention, i.e., the COTL1 protein, etc., present in a body fluid derived from a human test subject using the anti-COTL1 antibody, etc. prepared in the paragraph (1) (immunological assay methods) include enzyme immunoassay (ELISA and EIA), fluorescent immunoassay, radioimmunoassay (RIA), luminescent immunoassay, immunonephelometry, latex agglutination reaction, latex turbidimetry, hemagglutination reaction, particle agglutination reaction, and Western blotting.

When the method for measuring the marker for detecting gastric cancer of the present invention is carried out by immunoassay using a label, such as enzyme immunoassay, fluorescent immunoassay, radioimmunoassay, or luminescent immunoassay, it is preferred to immobilize the anti-COTL1 antibody, etc. or components in the sample onto a solid phase, followed by immunological reaction thereof. An insoluble carrier in the form of, for example, beads, a microplate, a test tube, a stick, or a test piece made of a material such as polystyrene, polycarbonate, polyvinyl toluene, polypropylene, polyethylene, polyvinyl chloride, nylon, polymethacrylate, latex, gelatin, agarose, cellulose, Sepharose, glass, metal, ceramics, or a magnetic substance can be used as a solid phase carrier. The immobilization can be performed by the binding between the solid phase carrier and the anti-COTL1 antibody, etc. or sample components according to a method known in the art such as a physical adsorption method, a chemical binding method, or combined use thereof.

In the present invention, the reaction of the anti-COTL1 antibody, etc. with the marker for detecting gastric cancer of the present invention derived from gastric cancer cells in the body fluid can be easily detected either directly by the labeling of the anti-COTL1 antibody, etc. or indirectly using a labeled secondary antibody. For the method for detecting gastric cancer of the present invention, it is preferred to use the latter indirect method (e.g., a sandwich method) in terms of sensitivity.

A labeling material such as peroxidase (POD), alkaline phosphatase, (3-galactosidase, urease, catalase, glucose oxidase, lactate dehydrogenase, amylase, or a biotin-avidin complex can be used for enzyme immunoassay; a labeling material such as fluorescein isothiocyanate, tetramethylrhodamine isothiocyanate, substituted rhodamine isothiocyanate, dichlorotriazine isothiocyanate, Alexa, or Alexa Fluoro can be used for fluorescent immunoassay; and a labeling material such as tritium, iodine 125, or iodine 131 can be used for radioimmunoassay. Alternatively, a labeling material such as $NADH^-$, $FMNH^{2-}$, luciferase system, luminol-hydrogen peroxide-POD system, acridinium ester system, or dioxetane compound system can be used for luminescent immunoassay.

A method known in the art for binding the labeling material to the antibody, such as a glutaraldehyde, maleimide, pyridyl disulfide, or periodic acid method, can be used for enzyme immunoassay, and a method known in the art therefor, such as a chloramine T or Bolton Hunter method can be used for radioimmunoassay. The assay procedures can be performed by a method known in the art (Current protocols in Protein Sciences, 1995, John Wiley & Sons Inc.; and Current protocols in Immunology, 2001, John Wiley & Sons Inc.).

For example, when the anti-COTL1 antibody, etc. is directly labeled, components in the body fluid are immobilized on a solid phase and contacted with the labeled anti-COTL1 antibody, etc. to form a complex between the marker for detecting gastric cancer (COTL1 protein, etc.) of the present invention and the anti-COTL1 antibody, etc. Then, unbound labeled antibodies are washed off, and the amount of the marker for detecting gastric cancer (COTL1 protein, etc.) in the body fluid can be measured on the basis of the amount of the labeled antibody bound or the amount of the labeled antibody unbound.

Alternatively, for example, when the labeled secondary antibody is used, the antibody of the present invention is reacted with the sample (primary reaction) and further reacted with the labeled secondary antibody (secondary reaction). These primary and secondary reactions may be performed in reverse order, may be performed simultaneously, or may be performed at a time interval. The primary and secondary reactions form a complex among the immobilized marker for detecting gastric cancer of the present invention, the anti-COTL1 antibody, etc., and the labeled secondary antibody or among the immobilized anti-COTL1 antibody, etc., the marker for detecting gastric cancer of the present invention, and the labeled secondary antibody. Then, unbound labeled secondary antibodies are washed off, and the mass of the marker for detecting gastric cancer in the sample can be measured on the basis of the amount of the labeled secondary antibody bound or the amount of the labeled secondary antibody unbound.

Specifically, for enzyme immunoassay, the labeling enzyme is reacted with a substrate under the optimum conditions, and the amount of the reaction product is measured by an optical method or the like. Alternatively, fluorescence intensity derived from the label of the fluorescent material and radioactivity derived from the label of the radioactive substance are measured for fluorescent immunoassay and radioimmunoassay, respectively. For luminescent immunoassay, the amount of luminescence from the luminescence reaction system is measured.

In the method of the present invention, the formation of agglutinated immune complexes through immunonephelometry, latex agglutination reaction, latex turbidimetry, hemagglutination reaction, particle agglutination reaction, or the like can be determined by the optical assay method of transmitted or scattered light thereof or by a visual observation assay method using, for example, a phosphate buffer, a glycine buffer, a tris buffer, a Good's buffer as a solvent. The reaction system may further contain a reaction promoter such as polyethylene glycol or a nonspecific reaction inhibitor.

A preferable embodiment of the detection method of the present invention will be shown below as an example. First, the antibody of the present invention is immobilized as a primary antibody on an insoluble carrier. Preferably, the antigen-unadsorbed surface of the solid phase is blocked with a protein (calf serum, bovine serum albumin, gelatin, etc.) irrelevant to the antigen. Subsequently, the immobilized primary antibody is contacted with a test sample. Then, the solid phase is contacted with a labeled secondary antibody that reacts, at a site different from that of the primary antibody, with the marker for detecting gastric cancer of the present invention. A signal from the label is detected. In this context, the "secondary antibody that reacts, at a site different from that of the primary antibody, with the marker for detecting gastric cancer" is not particularly limited as long as this antibody recognizes a site other than the binding site between the primary antibody and the marker for detecting gastric cancer (COTL1 protein, etc.). Any of a polyclonal antibody, antiserum, and a monoclonal antibody may be used, irrespective of the type of the immunogen. Alternatively, an antibody fragment (Fab, F(ab')$_2$, Fab, Fv, ScFv, etc.) thereof may be used. Moreover, several types of monoclonal antibodies may be used as such secondary antibodies.

On the contrary, the antibody of the present invention may be labeled and used as a secondary antibody. In this case, the antibody that reacts, at a site different from that of the antibody of the present invention, with the marker for detecting gastric cancer is immobilized as a primary antibody on an insoluble carrier, and this immobilized primary antibody is contacted with a test sample and subsequently contacted with the labeled antibody of the present invention as a secondary antibody. A signal from the label is used.

As described above, the antibody of the present invention specifically reacts with the marker for detecting gastric cancer derived from gastric cancer cells and as such, can be used as a drug for cancer detection. The detection drug of the present invention comprises the antibody of the present invention. Thus, the gastric cancer cell-derived marker for detecting gastric cancer contained in a sample collected from an individual suspected of having gastric cancer can be detected using the detection drug of the present invention to thereby detect gastric cancer affecting the individual.

Also, the detection drug of the present invention can be used in any means as long as immunological assay can be performed using this means. The detection drug of the present invention can be used in combination with convenient means known in the art such as a test strip for immunochromatography to thereby detect cancer more conveniently and rapidly. The test strip for immunochromatography comprises, for example: a sample-receiving portion made of a material easily absorbing a sample; a reagent portion containing the detection drug of the present invention; a developing portion in which a reaction product of the sample and the detection drug is transferred; a labeling portion in which the developed reaction product is colored; and a displaying portion to which the colored reaction product is developed. The test strip for immunochromatography can assume the same form as in a diagnostic drug for pregnancy. First, upon application of a sample to the sample-receiving portion, the sample-receiving portion absorbs the sample and allows the sample to reach the reagent portion. Subsequently, in the reagent portion, the gastric cancer cell-derived marker for detecting gastric cancer in the sample reacts with the anti-COTL1 antibody, etc. The reaction complex is transferred through the developing portion to reach the labeling portion. In the labeling portion, the reaction complex reacts with a labeled secondary antibody. When the reaction product with the labeled secondary antibody is developed to the displaying portion, a color is observed. The test strip for immunochromatography does not give its user any pain or risk associated with use of reagents and as such, can be used in at-home monitoring, the results of which can be scrutinized at each medical institution level for treatment (surgical resection, etc.) and linked to the prevention of metastasis or recurrence. Currently, this test strip can be produced inexpensively at a large scale by a production method as described in, for example, JP Patent Publication (Kokai) No. 10-54830A (1988). In addition, the detection drug of the present invention can be used in combination with a detection drug for a known tumor marker for gastric cancer to thereby achieve more highly reliable diagnosis.

2-2. Affection Determination Step

The "affection determination step" is the step of determining whether or not the test subject has gastric cancer on the basis of the amount of the protein measured in the measurement step of the marker for detecting gastric cancer. Whether or not the test subject has gastric cancer is determined on the basis of the measured mass of the marker for detecting gastric cancer, i.e., the COTL1 protein, etc. One example of a determination method include a method in which when the amount of the marker for detecting gastric cancer in the test subject is statistically significantly larger than that of a normal individual, the test subject is determined to have gastric cancer.

In this context, the "normal individual" refers to an individual at least unaffected with gastric cancer, preferably a healthy individual. The normal individual is further required to be of the same organism species as in the test subject. For example, when the test subject subjected to examination is a human (human test subject), the normal individual must also be a human (hereinafter, referred to as a "normal human individual" in the present specification). It is preferred for the normal individual to have the same or similar physical conditions as or to those of the test subject. The physical conditions of, for example, a human, correspond to race, sex, age, height, body weight, etc.

Examples of the phrase "statistically significantly" include the case in which the significance level of the obtained value is smaller than 5%, 1%, or 0.1%. Hence, the phrase "statistically significantly larger" means that the statistical manipulation of the quantitative difference between the markers for detecting gastric cancer obtained from the test subject and the normal individual, respectively, shows the significant difference therebetween in which the amount of the protein in the test subject is larger than that of the normal individual. The phrase "statistically significantly larger" usually corresponds to the case in which the amount of the marker for detecting gastric cancer in the body fluid of the test subject is larger than that of a normal individual by two or more times, preferably three or more times, more preferably four or more times, most preferably five or more times. The quantitative difference by three or more times can offer high reliability and can be statistically significantly larger. A test method known in the art capable of determining the presence or absence of significance can be used appropriately for testing the statistical manipulation without particular limitations. For example, a student's t test or a multiple comparison test can be used.

The amount of the marker for detecting gastric cancer in the body fluid of the normal individual can be measured preferably in the same way as the method for measuring the amount of the marker for detecting gastric cancer in the body fluid of the test subject described in the preceding step. The amount of the marker for detecting gastric cancer in the body fluid of the normal individual may be measured every time the amount of the marker for detecting gastric cancer in the body fluid of the test subject is measured. Alternatively, the amount of the marker for detecting gastric cancer may be measured in advance for use. Particularly, the mass of the marker for detecting gastric cancer is measured in advance under various physical conditions of normal individuals, and the values can be input to a computer for database. This approach is convenient because the physical conditions of the test subject can be input to the computer to thereby immediately utilize the amount of the marker for detecting gastric cancer derived from a normal individual having the optimum physical conditions for comparison with the test subject.

When the amount of the marker for detecting gastric cancer in the body fluid of the test subject is statistically significantly larger than that in the body fluid of the normal individual, the test subject is determined to have gastric cancer. In the present invention, the disease stage of targeted gastric cancer is not particularly limited and spans early gastric cancer to terminal gastric cancer. The present invention is of practical benefit, particularly because even early gastric cancer can be detected. The "early gastric cancer" refers to gastric cancer whose tumor is localized to its site of occurrence (in mucosa) without invasion to its neighboring tissue or with invasion, if any, limited to a narrow region. The early gastric cancer encompasses stages 0 and I in stage classification. The early detection of gastric cancer remarkably improves 5-year survival rates.

As described above, the method for detecting gastric cancer of the present invention involves immunologically assaying the marker for detecting gastric cancer in a body fluid sample using the antibody. The method of the present invention can not only determine whether or not a test subject has gastric cancer but also achieve the differentiation between gastric cancer patients and patients without gastric cancer.

3. Kit for Detecting Gastric Cancer

The third aspect of the present invention relates to a kit for detecting gastric cancer.

The "kit for detecting gastric cancer" refers to a kit that is directly or indirectly used to detect the presence or absence of gastric cancer affecting a test subject, the degree of affection, the presence or absence of improvement, or the degree of improvement or to screen for a candidate substance useful in the prevention, improvement, or treatment of gastric cancer.

The kit of the present aspect encompasses, as its constituent, a substance capable of specifically recognizing and binding to the COTL1 protein, preferably the protein having the amino acid sequence shown in SEQ ID NO: 1 or a variant sequence thereof, whose expression varies in a body fluid sample, particularly, blood, serum, or plasma in relation to gastric cancer affecting the test subject. Specifically, the kit comprises, for example, the anti-COTL1 protein antibody, etc. or the fragment thereof, or the chemically modified derivative thereof. These antibodies may be conjugated to a solid phase carrier. The kit may optionally contain, for example, a labeled secondary antibody and further, a substrate necessary for label detection, a carrier, a washing buffer, a sample diluent, an enzyme substrate, a reaction stopping solution, purified COTL1 protein, etc., serving as a standard, an instruction manual, etc.

EXAMPLES

The present invention will be described more specifically with reference to Examples below. However, the present invention is not intended to be limited to these Examples.

REFERENCE EXAMPLE (1) Preparation of Hollow-Fiber Filter 100 polysulfone hollow fibers having a pore size of approximately 50,000 in terms of molecular weight cutoff on the membrane surface were bundled, and both ends thereof were fixed to a glass tube using an epoxy potting agent so as not to clog the hollow portions of the hollow fibers, to prepare a minimodule. The minimodule (module A) is used for the removal of high-molecular-weight proteins in serum or plasma and has a diameter of approximately 7 mm and a length of approximately 17 cm. Likewise, a minimodule (module B) for use in the concentration of low-molecular-weight proteins was prepared using a membrane having a pore size of approximately 3,000 in terms of molecular weight cutoff. Each minimodule has, at one end, an inlet connected to the hollow fiber lumens and also has an outlet at the other end. The inlet and outlet of the hollow fibers form, together with a silicon tube, a passage of closed-circuit system in which a liquid is driven by a peristaltic pump to circulate. The glass tube serving as a jacket for the hollow fibers is equipped with a port for discharging a liquid leaked out of the hollow fibers to constitute one module set. The modules were connected via T-shaped connectors located in the middle of the passages to prepare one hollow-fiber filter comprising three modules A and one module B connected in tandem. This hollow-fiber filter was washed with distilled water and filled with an aqueous solution of PBS (phosphate buffer containing 0.15 mM NaCl, pH 7.4). Serum or plasma used as a fractionation material is injected to the passage inlet of the hollow-fiber filter and discharged from the passage outlet after fractionation and concentration. Each module A acts as a molecular sieve with a molecular weight cutoff of approximately 50,000 on the serum or plasma injected to the hollow-fiber filter, while lower-molecular-weight (smaller than 50,000) components are concentrated in the module B and prepared.

Example 1

(1) Identification of Protein in Blood of Normal Human Individuals and Gastric Cancer Patients A mixed solution of serum obtained from 6 patients of gastric cancer in their 50s to 70s and a mixed solution of serum obtained from 6 normal human individuals of age cohort were prepared. Each mixed solution was filtered through a filter with a pore size of 0.22 pin for removal of impurities to adjust its protein concentration to 50 mg/mL. This plasma was further diluted with a 25 mM ammonium bicarbonate solution (pH 8.0) into 12.5 mg/mL and fractionated on the basis of molecular weight through the hollow-fiber filter shown in Reference Example (1). The serum sample (total amount: 1.8 mL containing 250 μg of proteins at the maximum) thus fractionated was freeze-dried and then redissolved in 100 μL of a 25 mM ammonium bicarbonate solution (pH 8.0). This sample was subjected to peptide digestion with trypsin in an amount of 1/50 of the total protein amount under conditions of 37° C. for 2 to 3 hours and desalting treatment with a desalting column (Waters Corp.) and then further fractionated into 8 fractions using an ion-exchange column (KYA Technologies Corp.). Each of the fractions was further fractionated using a reverse-phase column (KYA Technologies Corp.), and the eluted peptides were assayed three times in a survey scan mode using a mass spectrometer Q-TOF Ultima (Micromass Ltd.) connected thereto online.

The analysis was conducted under conditions that can minimize protein misidentification using two criteria for blood protein identification: (i) at least one or more of peptides belonging to the protein was detected with high reliability having a P value of 0.05 or lower; and (ii) The measured values in MS data and MS/MS data of a peptide had an error of 0.3 daltons or lower from the theoretical value of the peptide.

This data was compared between the normal human individuals and the cancer patients to find, of the identified proteins, COTL1 protein as a protein whose average MASCOT score from three sample measurements of the gastric cancer patients was significantly higher than the average of the samples of the normal human individuals (Table 1).

TABLE 1

|  | Normal (1st) | Normal (2nd) | Normal (3rd) | Normal (average) | Gastric cancer (1st) | Gastric cancer (2nd) | Gastric cancer (3rd) | Gastric cancer (average) |
| --- | --- | --- | --- | --- | --- | --- | --- | --- |
| MASCOT score | 0 | 0 | 0 | 0 | 131 | 130 | 114 | 125 |

(2) Detection of COTL1 Protein in Blood by Western Blotting

Plasma samples were obtained from 16 gastric cancer patients (stage I: 7 individuals, stage III: 5 individuals, stage 1V: 4 individuals) and 12 normal controls. 100 μL of Affi-Gel Blue (Bio-Rad Laboratories, Inc.) and 50 μL, of Protein A-Sepharose (GE Healthcare) were added to 100 μL of each sample, and the mixture was reacted overnight at 4° C. to remove albumin and immunoglobulin in the sample. The sample thus obtained was subjected to solubilization treatment with an SDS sample buffer (50 mM tris-HCL, pH 6.8, 1 mM DTT, 5% SDS, 10% glycerol) and boiling treatment and applied to SDS-polyacrylamide gel (16%) electrophoresis, and proteins were then transferred to a PVDF membrane. This membrane was reacted with a rabbit polyclonal antibody (Proteintech Group Inc.) and further with a peroxidase-labeled secondary antibody. Proteins that showed immune response were visualized by exposure to an X-ray film using SuperSignal West Femto Maximum Sensitivity Substrate (Pierce Biotechnology, Inc.). The signal intensity of a band corresponding to COTL1 was digitalized by image analysis using Scion Image (Scion Corporation). As a result, a high plasma concentration of the COTL1 protein was detected in the early and advanced gastric cancer patients compared with the normal human controls (FIG. 1).

Comparative Example 1

(1) Comparison of Detecting Gastric Cancer Performance with CEA and CA19-9

CEA and CE19-9 were selected as tumor markers to be compared. CEA (carcinoembryonic antigen) is a tumor marker most frequently used in the widest range in clinical practice and is useful in the detection of gastric cancer as well as lung cancer, breast cancer, biliary cancer, pancreatic cancer, colon cancer, etc. On the other hand, CA19-9 is known to exhibit a high positive rate mainly in advanced cases of gastric cancer, colon cancer, and pancreatic cancer and gallbladder/bile duct cancer. Unfortunately, the markers are both low sensitive and are not suitable for the detection of early cancer.

Figure 2:
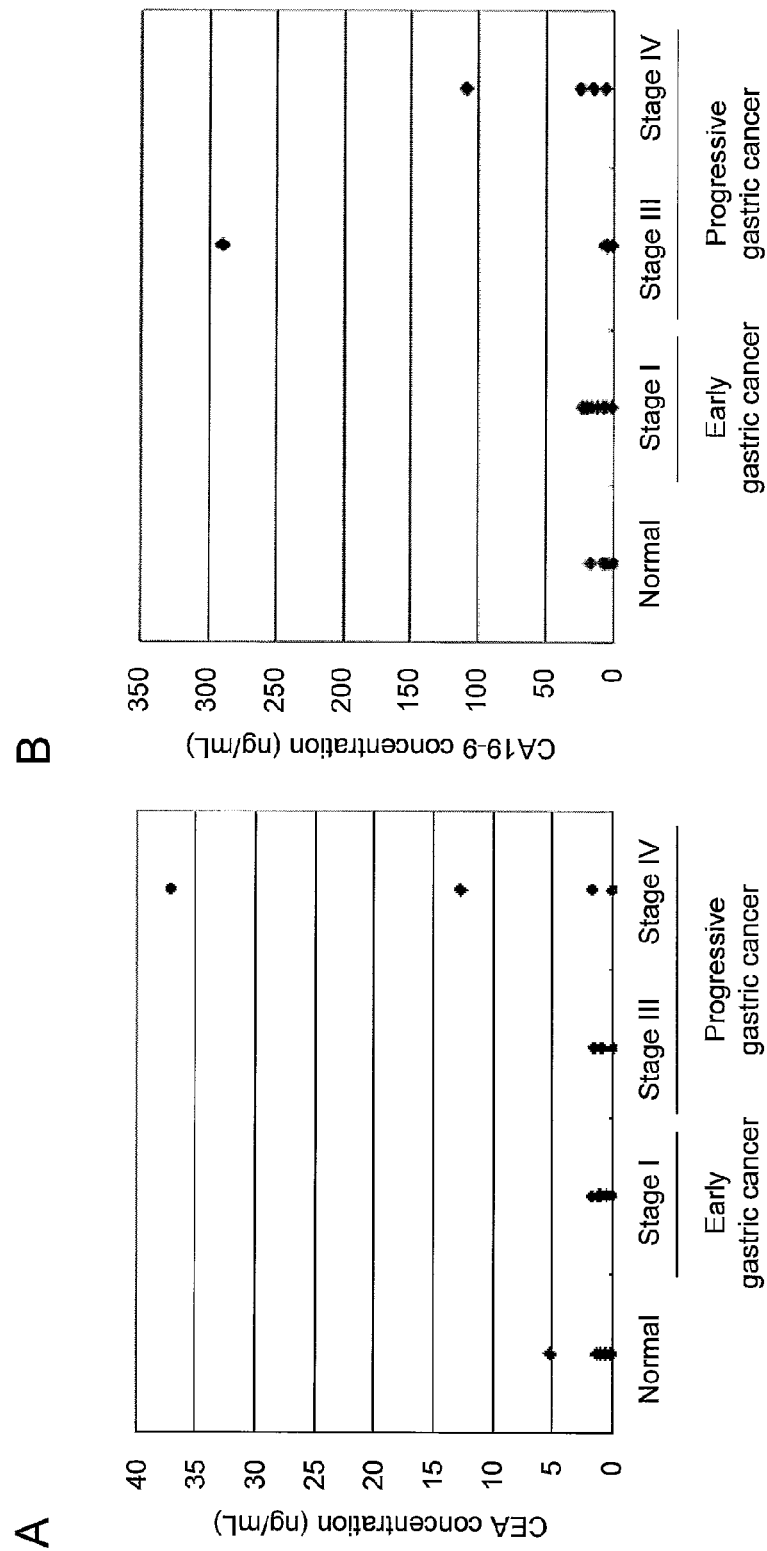
FIG. 2 is a graph showing results of detecting CEA (FIG. 2A) and CA19-9 (FIG. 2B) in the plasma of gastric cancer patients and normal human individuals by sandwich ELISA.

Plasma CEA levels in gastric cancer patients and normal controls were measured using a CagAg CEA EIA kit (Fujirebio Inc.) (FIG. 2A). CEA exhibits a high value only for stage 1V and cannot achieve the detection of early gastric cancer.

CA19-9 levels (FIG. 2B) were measured using a CagAg CA19-9 EIA kit (Fujirebio Inc.). CA19-9 exhibits a particularly high value in some samples from stage III and VI patients but cannot achieve the detection of early gastric cancer.

There results demonstrated that the method of the present invention was exceedingly excellent in detecting early gastric cancer.

INDUSTRIAL APPLICABILITY

According to the present invention, gastric cancer can be detected effectively by a simple and inexpensive method and can thus be detected, diagnosed, and treated early. In addition, the method of the present invention can detect gastric cancer noninvasively using the blood of patients and thus achieves the convenient and rapid detection of gastric cancer.

All publications, patents, and patent applications cited herein are incorporated herein by reference in their entirety.

---

SEQUENCE LISTING

```
<160> NUMBER OF SEQ ID NOS: 1

<210> SEQ ID NO 1
<211> LENGTH: 142
<212> TYPE: PRT
<213> ORGANISM: Homo sapiens

<400> SEQUENCE: 1

Met Ala Thr Lys Ile Asp Lys Glu Ala Cys Arg Ala Ala Tyr Asn Leu
1               5                   10                  15

Val Arg Asp Asp Gly Ser Ala Val Ile Trp Val Thr Phe Lys Tyr Asp
                20                  25                  30

Gly Ser Thr Ile Val Pro Gly Glu Gln Gly Ala Glu Tyr Gln His Phe
            35                  40                  45

Ile Gln Gln Cys Thr Asp Asp Val Arg Leu Phe Ala Phe Val Arg Phe
    50                  55                  60

Thr Thr Gly Asp Ala Met Ser Lys Arg Ser Lys Phe Ala Leu Ile Thr
65                  70                  75                  80

Trp Ile Gly Glu Asn Val Ser Gly Leu Gln Arg Ala Lys Thr Gly Thr
                85                  90                  95

Asp Lys Thr Leu Val Lys Glu Val Val Gln Asn Phe Ala Lys Glu Phe
            100                 105                 110

Val Ile Ser Asp Arg Lys Glu Leu Glu Glu Asp Phe Ile Lys Ser Glu
        115                 120                 125

Leu Lys Lys Ala Gly Gly Ala Asn Tyr Asp Ala Gln Thr Glu
    130                 135                 140
```

--- wherein the COTL1 protein is a polypeptide shown in SEQ ID NO: 1, wherein the variant is an amino acid sequence derived from the polypeptide shown in SEQ ID NO: 1 by the deletion, substitution, addition, or insertion of one or more amino acids, and that exhibits a percent identity to the polypeptide shown in SEQ ID NO: 1 of approximately 95% or higher, wherein if the amount of the marker for detecting gastric cancer in the test subject is statistically significantly larger than that of a normal individual, the test subject is determined to have gastric cancer, wherein the test subject is suspected of having gastric cancer, and wherein early stage gastric cancer is classified into stages 0 and/or I, and late stage gastric cancer is classified into stages II, III and/or IV.

2. The method according to claim 1, wherein the statistically significantly larger amount is two or more times that of a normal individual.

3. The method according to claim 1, wherein the measurement is performed using a substance capable of specifically binding to the marker for detecting gastric cancer.

4. The method according to claim 3, wherein the anti-COTL1 antibody is an anti-COTL1 variant antibody, and/or a fragment thereof.

5. The method according to claim 1, wherein the gastric cancer is early gastric cancer.

6. The method according to claim 1, wherein the body fluid sample is blood or urine.

* * * * *

---

The invention claimed is:

1. A method of indicating the potential presence of early stage gastric cancer comprising:
  detecting COTL1 (coactosin-like 1) protein, and/or a variant thereof as a marker for detecting gastric cancer by incubating an anti-COTL1 antibody with a body fluid derived from a test subject under conditions in which the anti-COTL1 antibody binds COTL1 protein, and/or a variant thereof,
  measuring in vivo the amount of COTL1 protein, and/or a variant thereof present in the body fluid derived from the test subject, by incubating an anti-COTL1 antibody with the body fluid under conditions in which the anti-COTL1 antibody binds COTL1 protein,
  correlating an increase amount of COTL1 protein, and/or a variant thereof as compared with a normal amount of COTL1 protein, and/or a variant thereof present in body fluid with the presence of gastric cancer, and
  determining whether or not the test subject has gastric cancer on the basis of the amount,